United States Patent [19]

Lawton et al.

[11] Patent Number: 4,757,069

[45] Date of Patent: Jul. 12, 1988

[54] PYRIDAZODIAZEPINE DERIVATIVES

[75] Inventors: Geoffrey Lawton, Hitchin; Sally Redshaw, Stevenage, both of England

[73] Assignee: Hoffmann-La Roche Inc., Nutley, N.J.

[21] Appl. No.: 124,749

[22] Filed: Nov. 24, 1987

[30] Foreign Application Priority Data

Dec. 15, 1986 [GB] United Kingdom ............... 8629875

[51] Int. Cl.$^4$ .................. A61K 31/33; A61K 31/50; C07D 403/04; C07D 401/04
[52] U.S. Cl. ................................. 514/221; 540/500
[58] Field of Search .................. 540/500; 514/221

[56] References Cited

U.S. PATENT DOCUMENTS 4,512,924  4/1985  Attwood et al. ............... 540/500
4,658,024  4/1987  Attwood et al. ............... 540/500
4,692,438  9/1987  Hassall et al. ............... 540/500

Primary Examiner—Robert T. Bond
Attorney, Agent, or Firm—Jon S. Saxe; Bernard S. Leon; Richard J. Mazza

[57] ABSTRACT

Compounds of the formula

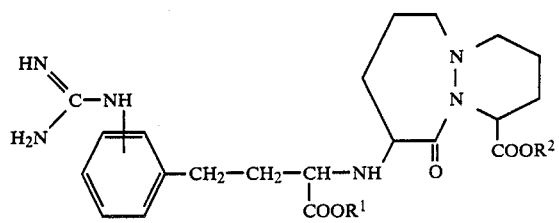

I wherein $R^1$ and $R^2$ each independently represent hydrogen, $C_1$–$C_{10}$-alkyl, adamantyl-($C_1$–$C_4$-alkyl) or ($C_2$–$C_6$-alkanoyloxy)-($C_1$–$C_4$-alkyl), and pharmaceutically acceptable salts thereof possess antihypertensive activity and can be used as theraputic or prophylactic agents in pharmaceutical preparations. Intermediates for the production of such compounds are also provided.

39 Claims, No Drawings

PYRIDAZODIAZEPINE DERIVATIVES

DESCRIPTION OF THE INVENTION

The present invention is concerned with pyridazodiazepine derivatives, pharmaceutical preparations containing such derivatives as a therapeutic agent, and a method of treating or preventing hypertension using such derivative compounds.

The pyridazodiazepine derivatives of the present invention are compounds of the formula

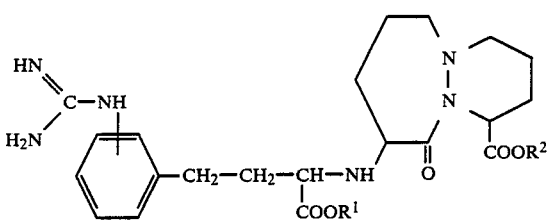

wherein $R^1$ and $R^2$ each independently are hydrogen, $C_1$–$C_{10}$-alkyl, adamantyl-($C_1$–$C_4$-alkyl) or ($C_2$–$C_6$-alkanoyloxy)-($C_1$–$C_4$-alkyl), as well as pharmaceutically acceptable salts thereof.

The compounds of formula I contain three asymmetric carbon atoms and can therefore exist as optically pure diastereoisomers, as diastereoisomeric racemates or as mixtures of different diastereoisomeric racemates. The present invention includes within its scope all of these possible forms. In the compounds of formula I the configuration at each of the asymmetric carbon atoms is preferably (S).

As used throughout this disclosure, the terms "$C_1$–$C_4$-alkyl" and "$C_1$–$C_{10}$-alkyl" mean straight-chain or branched-chain alkyl groups which contain the respective number of carbon atoms. Examples of such alkyl groups include methyl, ethyl, propyl, isopropyl, butyl, tert.butyl, n-pentyl, n-hexyl, n-heptyl, n-octyl, n-nonyl, n-decyl, and the like. The term "$C_2$–$C_6$-alkanoyloxy" means an alkanoyloxy group derived from a straight-chain or branched-chain alkanecarboxylic acid containing up to 6 carbon atoms (for example, acetic acid, propionic acid, butyric acid, pivalic acid, and so forth).

The compounds of formula I form pharmaceutically acceptable salts with acids. Examples of such salts are mineral acid salts such as hydrohalides (for example, hydrobromides, hydrochlorides, and so forth), sulphates, phosphates, nitrates, and so forth, and organic acid salts such as acetates, maleates, fumarates, tartrates, citrates, salicylates, methanesulphonates, p-toluenesulphonates, and so forth. The compounds of formula I in which $R^1$ and/or $R^2$ are hydrogen also form pharmaceutically acceptable salts with bases. Examples of such salts are alkali metal salts (for example, sodium and potassium salts), alkaline earth metal salts (for example, calcium and magnesium salts), ammonium salts and salts with organic amines (for example, dicyclohexylamine salts).

In formula I above, $R^1$ preferably is hydrogen, $C_1$–$C_{10}$-alkyl or adamantyl-$C_1$–$C_4$-alkyl), especially hydrogen, ethyl, n-decyl or 1-adamantylethyl. $R^2$ preferably is hydrogen or ($C_2$–$C_6$-alkanoyloxy)-($C_1$–$C_4$-alkyl), especially hydrogen or pivaloyloxymethyl. With respect to the guanidino group $H_2N$—$C(NH)$—NH in the compounds of formula I, this is preferably situated in the para-position of the phenyl ring.

As will be evident from the foregoing, especially preferred pyridazodiazepine derivatives provided by the present invention are those in which $R^1$ is hydrogen, ethyl, n-decyl or 1-adamantylethyl, $R^2$ is hydrogen or pivaloyloxymethyl, and the guanidino group is present in the para-position of the phenyl ring.

The most preferred pyridazodiazepine derivatives provided by the present invention are 9(S)-[1(S)-carboxy-3-(4-guanidinophenyl)propylamino]-octahydro-10-oxo-6H-pyridazo[1,2-a][1,2]diazepine-1(S)-carboxylic acid and its pharmaceutically acceptable salts, particularly the dihydrobromide.

Examples of other interesting pyridazodiazepine derivatives of the present invention are:

9(S)-[1(S)-Ethoxycarbonyl-3-(4-guanidinophenyl)-propylamino]-octahydro-10-oxo-6H-pyridazo[1,2-a][1,2]diazepine-1(S)-carboxylic acid, 9(S)-[1(S)-(n-decyloxycarbonyl)-3-(4-guanidinophenyl)-propylamino]-octahydro-10-oxo-6H-pyridazo[1,2-a][1,2]diazepine-1(S)-carboxylic acid, 9(S)-[1(S)-[[2-(1-adamantyl)ethoxy]carbonyl]-3-(4-guanidinophenyl)propylamino]-octahydro-10-oxo-6H-pyridazo[1,2-a][1,2]diazepine-1(S)-carboxylic acid, and 9(S)-[1(S)-ethoxycarbonyl-3-(4-guanidinophenyl)-propylamino]-octahydro-10-oxo-6H-pyridazo[1,2-a][1,2]diazepine-1(S)-carboxylic acid pivaloylxymethyl ester, as well as their pharmaceutically acceptable salts.

Compounds of formula I and their pharmaceutically acceptable salts are can be prepared by (a) catalytically hydrogenating a compound of the formula

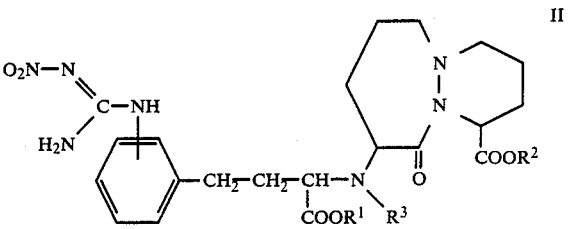

wherein $R^1$ and $R^2$ have the same meaning given above, and $R^3$ is hydrogen or benzyl, in an acidic medium and converting any resulting non-pharmaceutically acceptable acid addition salt of a compound of formula I into a compound of formula I, or (b) for the preparation of a compound of formula I in which $R^1$ and/or $R^2$ are hydrogen, treating a compound of formula I in which $R^1$ and/or $R^2$ are $C_1$–$C_{10}$-alkyl with an acid and/or a base, or (c) if desired, separating a mixture of diastereoisomeric racemates into the diastereoisomeric racemates of optically pure diastereoisomers, or (d) if desired, resolving a racemate obtained into the optical antipodes, or (e) if desired, converting a compound of formula I obtained into a pharmaceutically acceptable salt or converting a pharmaceutically acceptable acid addition salt of a compound of formula I obtained into a compound of formula I.

The catalytic hydrogenation of a compound of formula II in an acidic medium in accordance with embodiment (a) of the process yields an acid addition salt of a compound of formula I. The catalytic hydrogenation can be carried out, for example, in the presence of a platinum or palladium catalyst which may be supported on an inert carrier material. Palladium-on-carbon is an especially suitable catalyst. The catalytic hydrogenation is preferably carried out in an acidic medium which yields a pharmaceutically acceptable acid addition salt of a compound of formula I, conveniently a suitable alkanecarboxylic acid such as acetic acid, aqueous hydrochloric acid, aqueous hydrobromic acid or a mixture of one of these aqueous acids with a lower alkanecarboxylic acid. In a further embodiment, the acidic medium may be provided, at least partially, by using an acid addition salt of the compound of formula II. Conveniently, the catalytic hydrogenation is carried out at about room temperature and under atmospheric pressure.

When the catalytic hydrogenation yields a non-pharmaceutically acceptable acid addition salt of a compound of formula I, this salt is converted into a compound of formula I. This conversion can be carried out by treatment with a base under conditions that will be apparent to those skilled in the art.

According to embodiment (b) of the process, a compound of formula I in which $R^1$ and/or $R^2$ are $C_1$-$C_{10}$-alkyl is converted into a compound of formula I in which $R^1$ and/or $R^2$ are hydrogen by treatment with an acid and/or a base, as the case may require depending on the nature of the $C_1$-$C_{10}$-alkyl group. This embodiment can be carried out, for example, when $R^1$ and/or $R^2$ are tert.-butyl, by treatment with an appropriate acid such as hydrogen bromide in acetic acid or trifluoroacetic acid, advantageously at about room temperature. Again, for example, when $R^1$ and/or $R^2$ are $C_1$-$C_{10}$-alkyl other than tert.butyl, the treatment can be carried out using an appropriate base such as an aqueous ethanolic alkali metal hydroxide (for example, aqueous ethanolic sodium hydroxide or aqueous ethanolic potassium hydroxide) or aqueous ammonia at a temperature between about room temperature and the boiling point of the reaction mixture, advantageously at about room temperature.

The separation of a mixture of diastereoisomeric racemates into the diastereoisomeric racemates or optically pure diastereoisomers in accordance with embodiment (c) of the process can be carried out, for example, by chromatography (such as on silica gel) using a suitable solvent system (such as ethyl acetate/n-hexane, toluene-/ethyl acetate, and the like).

The resolution of a racemate into the optical antipodes in accordance with embodiment (d) of the process can be carried out, for example, by treatment with an appropriate optically active acid or base as the case may require, separating the optically active salts obtained (for instance, by fractional crystallization) and, where required, liberating the optically uniform compounds from these salts by conventional techniques.

The conversion of a compound of formula I into a pharmaceutically acceptable salt in accordance with embodiment (e) of the process can be carried out in a manner known per se by treatment with an appropriate acid or, where $R^1$ and/or $R^2$ in the compound of formula I are hydrogen, by treatment with an appropriate base. The conversion of a pharmaceutically acceptable acid addition salt of a compound of formula I into a compound of formula I, also in accordance with embodiment (e) of the process, can be carried out by treatment with an appropriate base.

The compounds of formula II which are used as starting materials can be prepared, for example, by reacting a compound of the formula

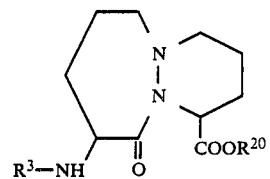

wherein $R^3$ represents hydrogen or benzyl and $R^{20}$ represents $C_1$-$C_{10}$-alkyl, with a compound of the formula

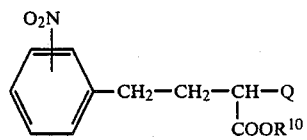

wherein $R^{10}$ is $C_1$-$C_{10}$-alkyl and Q is a leaving atom or group, to give a compound of the formula

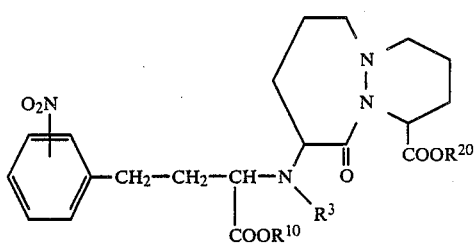

wherein $R^3$, $R^{10}$ and $R^{20}$ have the same meanings as given above, and, if desired, treating a compound of formula V with an acid and/or a base to give a compound of the formula

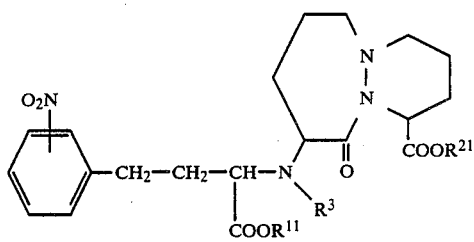

wherein $R^3$ has the meaning given above and $R^{11}$ and/or $R^{21}$ are hydrogen, and, also if desired, esterifying a compound of formula VI to give a compound of the formula

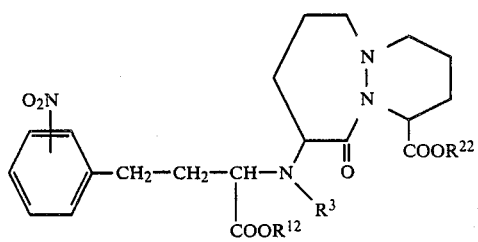

wherein $R^3$ has the meaning given above and $R^{12}$ and/or $R^{22}$ are $C_1$-$C_{10}$-alkyl (other than the $C_1$-$C_{10}$-alkyl denoted by $R^{10}$ and $R^{20}$ in formula V), adamantyl-($C_1$-$C_4$-alkyl) or ($C_2$-$C_6$-alkanoyloxy)-($C_1$-$C_4$-alkyl).

The leaving atom or group denoted by Q in a compound of formula IV can be any conventional leaving atom or group; for example, a halogen atom such as a bromine atom or a sulphonate group of the formula —O—SO$_2$Y in which Y is a methyl, trifluoromethyl, p-tolyl, 4-nitrophenyl, or the like.

The reaction of a compound of formula III with a compound of formula IV to give a compound of formula V can be carried out in a known manner, conveniently in the presence of an inert organic solvent such as acetonitrile, dimethyl sulphoxide, dimethylformamide, or the like, and in the presence of an acid-binding agent such as an alkali metal carbonate (for example, sodium carbonate), a basic ion-exchange resin or, preferably, a tertiary organic base (for example, triethylamine). The reaction can be carried out at a temperature from about 0° C. up to the boiling point of the reaction mixture.

The treatment of a compound of formula V with an acid and/or a base to give a compound of formula VI can be carried out in a manner known per se. The particular treatment which is required will, of course, depend on the nature of the $C_1$-$C_{10}$-alkyl groups present in the compound of formula V. For example, when $R^{10}$ and/or $R^{20}$ are tert.butyl, the treatment can be carried out using an appropriate acid such as anhydrous trifluoroacetic acid, conveniently at about room temperature, or hydrogen bromide in acetic acid, also conveniently at about room temperature. Again, for example, when $R^{10}$ and/or $R^{20}$ are $C_1$-$C_{10}$-alkyl other than tert.butyl the treatment can be carried out using an appropriate base such as an aqueous ethanolic alkali metal hydroxide (for instance, aqueous ethanolic sodium hydroxide or aqueous ethanolic potassium hydroxide) or aqueous ammonia at a temperature between about room temperature and the boiling point of the reaction mixture, most advantageously at about room temperature.

The esterification of a compound of formula VI to give a compound of formula VII can be carried out, for example, by treatment of the compound of formula VI with a suitable alkanol or appropriately substituted alkanol in the presence of N,N'-dicyclohexylcarbodiimide. Again, for example, a compound of formula VI in which $R^3$ is benzyl can be esterified by treatment with a suitable alkyl bromide or appropriately-substituted alkyl bromide in the presence of a strong base (for instance, potassium hydroxide) or cesium carbonate.

Subsequently, a compound of formula V, VI or VII is reduced to give a compound of the formula

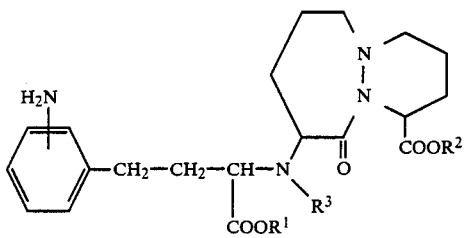

VIII wherein $R^1$, $R^2$ and $R^3$ have the meanings given above.

The reduction of a compound of formula V, VI or VII to give a compound of formula VIII can be carried out, for example, by catalytic hydrogenation in the presence of a noble metal catalyst such as platinum or palladium which may be supported on an inert carrier material. Palladium-on-carbon can be mentioned as an especially suitable catalyst for the present purpose. This catalytic hydrogenation is advantageously carried out in an inert organic solvent, particularly an alkanol such as methanol, ethanol and so forth, at room temperature and under atmospheric pressure. Again, for example, the reduction can be carried out using zinc/acetic acid according to known techniques.

A compound of formula VIII in which $R^1$ and/or $R^2$ are $C_1$-$C_{10}$-alkyl can, if desired, be converted into a compound of formula VIII in which $R^1$ and/or $R^2$ are hydrogen by treatment with an acid and/or a base. This treatment can be carried out in the same manner as described earlier in connection with the conversion of a compound of formula V into a compound of formula VI.

A compound of formula VIII is subsequently reacted with 1-nitroguanyl-3,5-dimethylpyrazole to give a compound of formula II.

The reaction of a compound of formula VIII with 1-nitroguanyl-3,5-dimethylpyrazole can be carried out in the presence of an inert organic solvent, particularly an alkanol such as methanol, ethanol, or the like, and at an elevated temperature, preferably at the reflux temperature of the reaction mixture.

A compound of formula II in which $R^1$ and/or $R^2$ are $C_1$-$C_{10}$-alkyl can, if desired, be converted into a compound of formula II in which $R^1$ and/or $R^2$ are hydrogen by treatment with an acid and/or a base. This treatment can be carried out in the same manner as described earlier in connection with the conversion of a compound of formula V into a compound of formula VI.

The compounds of formulae II, V, VI, VII and VIII which can be represented collectively by the formula

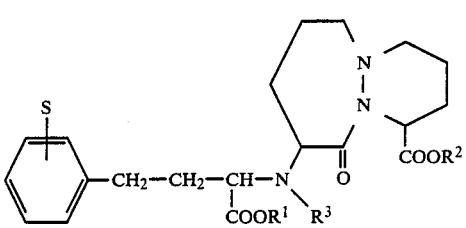

IX wherein $R^1$, $R^2$ and $R^3$ have the meanings given earlier and S is nitro, amino or 2-nitroguanidino, form part of the present invention.

The compounds of formula III in which $R^3$ is hydrogen are known compounds or analogs of known compounds. The compounds of formula III in which $R^3$ is benzyl can be prepared by reductively benzylating a compound of formula III in which $R^3$ is hydrogen.

The compounds of formula IV are known compounds or analogs of known compounds.

The pyridazodiazepine derivatives provided by the present invention inhibit angiotensin converting enzyme (ACE) which brings about the conversion of angiotensin I into angiotensin II and are therefore useful as antihypertensive agents. Moreover, they have an unexpectedly prolonged duration of activity.

The activity of the present pyridazodiazepine derivatives in inhibiting angiotensin-converting enzyme in vitro can be determined using the test now described.

The method used is based on the method of Santos, R. A. S., Kreiger, E. M., and Greene L. J., Hypertension (1985), 7, 244–252. Angiotensin converting enzyme (rabbit lung) is incubated in the presence or absence of various concentrations of a test substance for 90 minutes at 37° C. in 0.1M potassium phosphate buffer, pH 7.5, containing 30 mmol of sodium chloride. If the test substance is an ester, it is cleaved by treatment with hog liver esterase prior to carrying out the test. The reaction is initiated by adding angiotensin I to a final concentration of 250 μmol. The final volume of the reaction mixture is 0.25 ml. After holding the reaction mixture at 37° C. for 30 minutes the reaction is terminated by adding 1.45 ml of 0.3M sodium hydroxide solution. 100 ml of a 0.2% (weight/volume) solution of o-phthaldialdehyde in methanol are added and, after 10 minutes, the solution is acidified with 200 μl of 3M hydrochloric acid. The resulting solution is then subjected to fluorescence spectrometry using excitation and emission wavelengths of 365 nm and 500 nm, respectively, and the $IC_{50}$ value is calculated. The $IC_{50}$ is that concentration of test substance which reduces by 50% the conversion of angiotensin I into angiotensin II.

In the test described above, 9(S)-[1(S)-carboxy-3-(4-guanidinophenyl)propylamino]-octahydro-10-oxo-6H-pyridazo[1,2-a][1,2]diazepine-1(S)-carboxylic acid dihydrobromide exhibits an $IC_{50}$ of 0.6 nmol.

The pyridazodiazepine derivatives of the present invention can be used as therapeutic substances in the form of pharmaceutical preparations which contain them in association with a compatible pharmaceutical carrier material. This carrier material can be an organic or inorganic carrier material which is suitable for enteral (for example, oral) or parenteral administration. Examples of such carrier materials are water, gelatin, gum arabic, lactose, starch, magnesium stearate, talc, vegetable oils, polyalkylene glycols and petroleum jelly. The pharmaceutical preparations can be made up in solid form (for example, as tablets, dragees, suppositories or capsules) or in a liquid form (for example, as solutions, suspensions or emulsions). The pharmaceutical preparations may be subjected to standard pharmaceutical operations such as sterilization and/or may contain adjuvants such as preserving, stabilizing, wetting or emulsifying agents, salts for varying the osmotic pressure, or buffers. The pharmaceutical preparations may also contain other therapeutically useful substances.

The pyridazodiazepine derivatives provided by the present invention can be administered to adults in a daily dosage from about 0.1 mg to 100 mg, preferably about 1 mg to 50 mg, per kilogram of body weight. The daily dosage may be administered as a single dose or in divided doses. It will be appreciated that the aforementioned dosage range is given by way of illustration only and can be varied upwards or downwards depending on factors such as the particular derivative being administered, the route of administration, the severity of the indication being treated and the condition of the patient as determined by the attending physician.

The compounds of formula IX in which $R^3$ is hydrogen also inhibit angiotensin-converting enzyme and can be used as antihypertensives.

The following Examples further illustrate the present invention:

EXAMPLE 1

A solution of 0.70 g of 9(S)-[1(S)-carboxy-3[4-(2-nitroguanidino)phenyl]propylamino]-octahydro-10-oxo-6H-pyridazo[1,2-a][1,2]diazepine-1(S)-carboxylic acid hydrobromide in a mixture of 16 ml of acetic acid, 4 ml of water and 4 drops of hydrobromic acid was hydrogenated over 10% palladium-on-carbon at room temperature and under atmospheric pressure for 72 hours. The catalyst was removed by filtration and the filtrate was evaporated. The residual oil was dissolved in 50 ml of water and the solution was lyophilized to give 0.735 g of 9(S)-[1(S)-carboxy-3-(4-guanidinophenyl)propylamino]-octahydro-10-oxo-6H-pyridazo[1,2-a][1,2]diazepine-1(S)-carboxylic acid dihydrobromide as an off-white amorphous solid.

NMR: $\delta_H$ (CD$_3$OD, 300 MHz): 1.44 (1H, m), 1.68–1.98 (4H, m), 2.04–2.36 (4H, m), 2.42 (1H, m), 2.63 (1H, m), 2.82–2.98 (2H, m), 3.04 (1H, broad, d), 3.17 (1H, m), 3.48 (1H, m), 4.01 (1H, t), about 4.90 (2H, obscured), 7.25 (2H, d) and 7.41 (2H, d).

MS: m/e 447 (20% [M+H]$^+$) and 211 (100).

The 9(S)-[1(S)-carboxy-3-[4-(2-nitroguanidino)phenyl]propylamino]-octahydro-10-oxo-6H-pyridazo[1,2-a][1,2]diazepine-1(S)-carboxylic acid hydrobromide used as the starting material was prepared as follows:

(A)(i) A solution of 0.566 g of tert.butyl 9(S)-amino-octahydro-10-oxo-6H-pyridazo[1,2-a][1,2]diazepine-1(S)-carboxylate, 0.688 g of tert.butyl 2(R,S)-bromo-4-(4-nitrophenyl)butanoate and 0.202 g of triethylamine in 12 ml of acetonitrile was heated to 80° C. for 16 hours. The solvent was removed by evaporation and the residue was partitioned between water and dichloromethane. The organic solution was evaporated and the resulting oil was chromatographed on silica gel. Elution with toluene/ethyl acetate (1:1) gave 0.195 g of tert.butyl 9(S)-[1(R)-tert.butoxycarbonyl-3-(4-nitrophenyl)propylamino]-octahydro-10-oxo-6H-pyridazo[1,2-a][1,2]diazepine-1(S)-carboxylate as a yellow oil and, subsequently, 0.252 g of tert.butyl 9(S)-[1(S)-tert.butoxycarbonyl-3-(4-nitrophenyl)propylamino]-octahydro-10-oxo-6H-pyridazo[1,2-a][1,2]diazepine-1(S)-carboxylate as a yellow oil.

Analysis for $C_{28}H_{42}N_4O_7$: Calculated: C: 61.5; H: 7.70; N: 10.25%. Found: C: 61.5; H: 7.75; N: 10.20%.

A(ii)(a) A solution of 18 g of 2(R)-hydroxy-4-phenylbutanoic acid in 200 ml of dichloromethane containing 20.5 g of triethylamine and 250 mg of 4-(dimethylamino)pyridine was stirred at room temperature and treated dropwise with 12 g of acetic anhydride. The resulting mixture was stirred for a further 3 hours and then acidified by the addition of 125 ml of 2N sulphuric acid. The organic phase was separated and washed with two 100 ml portions of 2N sulphuric acid, then with 100 ml of water and finally with 100 ml of saturated sodium chloride solution, dried over anhydrous magnesium sulphate and evaporated in vacuo to give 22 g of 2(R)-acetoxy-4-phenylbutanoic acid as a colouless viscous oil; $[\alpha]_{436}^{20} = +13.7°$ (c=1 in ethanol).

(b) A solution of 22 g of 2(R)-acetoxy-4-phenylbutanoic acid in 10 ml of glacial acetic acid was added dropwise to a cooled (−5° C.) and stirred nitrating mixture, prepared by the dropwise addition of 12.6 g of fuming 95% nitric acid to 41 g of acetic acid while maintaining the internal temperature at about 5° C. throughout by means of an external cooling bath (−10° C. to −5° C.) and finally allowing the temperature of the nitrating mixture to fall to −5° C. The resulting mixture was stirred at −5° C. for a further 2 hours, poured into about 200 ml of ice-water and stirred for several hours. The mixture was extracted with three 100 ml portions of diethyl ether, the combined organic extracts were washed with three 100 ml portions of water and with 100 ml of saturated sodium chloride solution, dried over anhydrous magnesium sulphate and evaporated in vacuo to give 27 g of a pale yellow oil consisting of a mixture of 2(R)-acetoxy-4-(2-nitrophenyl)-butanoic acid and 2(R)-acetoxy-4-(4-nitrophenyl)-butanoic acid in the approximate ratio 1:2 as determined by $^1$H-NMR spectroscopy. This oil was dissolved in 50 ml of warm toluene and left to crystallize for several hours at 0°–5° C. to give 9.6 g of 2(R)-acetoxy-4-(4-nitrophenyl)butanoic acid as a colorless crystalline solid having a melting point of 108°–109° C.

(c) 8.0 g of 2(R)-acetoxy-4-(4-nitrophenyl)butanoic acid were added portionwise to a stirred solution of 4 g of tert.butanol, 7 g of N,N'-dicyclohexylcarbodiimide and 450 mg of 4-pyrrolidinopyridine in 200 ml of dichloromethane and the mixture was stirred at 0° C. for 16 hours. The mixture was filtered and the filtrate was washed in succession with 100 ml of water, two 100 ml portions of 2N acetic acid, 100 ml of water, two 100 ml portions of saturated sodium bicarbonate solution and 100 ml of saturated sodium chloride solution, dried over anhydrous magnesium sulphate and evaporated in vacuo to give 10 g of a pale yellow semi-solid residue. This residue was triturated with a small amount of diethyl ether and filtered, and the filtrate was eluted through a silica gel column with diethyl ether/n-hexane (1:1) to give 9 g of tert.butyl 2(R)-acetoxy-4-(4-nitrophenyl)butanoate as a pale yellow oil; MS m/e 324 (10%, [M+H]+) and 268 (100%).

(d) 8.0 g of tert.butyl 2(R)-acetoxy-4-(4-nitrophenyl)-butanoate were dissolved in 200 ml of methanol saturated with ammonia at 0° C. and the mixture was stirred for 16 hours. Evaporation of the mixture in vacuo gave 7 g of an almost colorless oil which was dissolved in an equal volume of diethyl ether/n-hexane (1:1) and eluted through a silica gel column with the same solvent mixture to give 6 g of tert.butyl 2(R)-hydroxy-4-(4-nitrophenyl)butanoate as a colorless crystalline solid having a melting point of 41°–42° C.

(e) A solution of 0.4 ml of dry pyridine in 20 ml of dichloromethane (dried over molecular sieve) was cooled to −20° C. while stirring under anhydrous conditions and then treated dropwise with 1.4 g of trifluoromethanesulphonic anhydride. After 5 minutes a solution of 1.4 g of tert.butyl 2(R)-hydroxy-4-(4-nitrophenyl)butanoate in 5 ml of dry dichloromethane was added and the resulting mixture was stirred at 0° C. for 16 hours. The mixture was filtered through a silica gel column and the column was washed with two 10 ml portions of dry dichloromethane. The combined filtrates, containing tert.butyl 2(R)-trifluoromethanesulphonyloxy-4-(4-nitrophenyl)butanoate, were treated with 0.5 g of dry triethylamine and 1.4 g of tert.butyl 9(S)-amino-octahydro-10-oxo-6H-pyridazo[1,2-a][1,2]diazepine-1(S)-carboxylate and the mixture was stirred at room temperature for 1 hour. The mixture was washed in succession with 25 ml of water, 25 ml of saturated sodium bicarbonate solution and 25 ml of saturated sodium chloride solution, dried over anhydrous magnesium sulphate and evaporated in vacuo to give 3 g of a yellow oil. Chromatography on silica gel using diethyl ether for the elution gave 1.7 g (60%) of tert.butyl 9(S)-[1(S)-tert.butoxycarbonyl-3-(4-nitrophenyl)propylamino]-octahydro-10-oxo-6H-pyridazo[1,2-a][1,2]diazepine-1(S)-carboxylate as a yellow oil which was identical with the compound obtained according to the procedure described in paragraph (A)(i).

(A)(iii)(a) A solution of 2.8 g of tert.butyl 2(R)-hydroxy-4-(4-nitrophenyl)butanoate, prepared as described in paragraph (A)(ii)(d), and 2 ml of dry triethylamine in 20 ml of dry dichloromethane were added dropwise to a stirred solution, cooled to 0° C., of 2.2 g of 4-nitrobenzenesulphonyl chloride in 40 ml of dry dichloromethane and the mixture was stirred at 0° C. for 16 hours. The resulting solution was washed in succession with 50-ml of water, three 50 ml portions of 1N sulphuric acid, 50-ml of water, two 50 ml portions of saturated sodium bicarbonate solution and 50 ml of saturated sodium chloride solution, dried over anhydrous magnesium sulphate and evaporated in vacuo to give 4.7 g of a pale yellow gum. Trituration of this gum in 10 ml of diethyl ether gave 3.8 g (82%) of tert.butyl 4-(4-nitrophenyl)-2(R)-[(4-nitrophenyl)sulphonyloxy]-butanoate as a pale yellow crystalline solid having a melting point of 97°–98° C.

(b) 2 g of tert.butyl 9(S)-amino-octahydro-10-oxo-6H-pyridazo[1,2-a][1,2]diazepine-1(S)-carboxylate were added to a solution of 3.3 g of tert.butyl 4-(4-nitrophenyl)-2(R)-[(4-nitrophenyl)sulphonyloxy]butanoate and 1 ml of dry triethylamine in 50 ml of dry acetonitrile and the mixture was heated under reflux for 20 hours. The resulting solution was evaporated in vacuo, and the oily residue was dissolved in 50 ml of dichloromethane and washed in succession with two 50 ml portions of water, 50 ml of saturated sodium bicarbonate solution and 50 ml of saturated sodium chloride solution, dried over anhydrous magnesium sulphate and evaporated in vacuo to give 4 g of a yellow oil. Chromatography on silica gel using diethyl ether for the elution gave 2.7 g (70%) of tert.butyl 9(S)-[1(S))-tert.butoxycarbonyl-3-(4-nitrophenyl)propylamino]octahydro-10-oxo-6H-pyridazo[1,2-a][1,2]diazepine-1(S)-carboxylate as a yellow oil which was identical with the compound obtained according to the procedure described in paragraph (A)(i).

(B) A solution of 4.63 g of tert.butyl 9(S)-[1(S)-tert.butoxycarbonyl-3-(4-nitrophenyl)propylamino]-octahydro-10-oxo-6H-pyridazo[1,2-a][1,2]diazepine-1(S)-carboxylate in 100 ml of ethanol was hydrogenated over 10% palladium-on-carbon for 3 hours at room temperature and under atmospheric pressure. The catalyst was removed by filtration and the filtrate was evaporated. The resulting yellow oil was dissolved in 40 ml of ethanol, 1.72 g of 1-nitroguanyl-3,5-dimethyl-pyrazole were added, and the solution was heated under reflux for 48 hours. The solvent was removed by evaporation and the resulting oil was chromatographed on silica gel. Elution with 3% methanol in diethyl ether followed by crystallization from ethyl acetate/n-hexane gave 1.66 g of tert.butyl 9(S)-[1(S)-tert.butoxycarbonyl-3-[4-(2-nitroguanidino)phenyl]propylamino]-octahydro-10-oxo-6H-pyridazo[1,2-a][1,2]diazepine-1(S)-carboxylate as an off-white solid.

Analysis for $C_{29}H_{45}N_7O_7$: Calculated: C: 57.7; H: 7.5; N: 16.20%; Found: C: 57.7; H: 7.5; N: 15.95%.

(C)(i) A solution of 0.182 g of tert.butyl 9(S)-[1(S)-tert.butoxycarbonyl-3-[4-(2-nitroguanidino)phenyl]-propylamino]-octahydro-10-oxo-6H-pyridazo[1,2-a][1,2]diazepine-1(S)-carboxylate in 0.6 ml of acetic acid was treated with 1.8 ml of 45% hydrogen bromide in acetic acid and the solution was stirred for 1.25 hours at 20° C. The solution was poured into 100 ml of anhydrous diethyl ether, stirred for 2 hours and then filtered to give 0.17 g of 9(S)-[1(S)-carboxy-3-[4-(2-nitroguanidino)phenyl]propylamino]-octahydro-10-oxo-6H-pyridazo[1,2-a][1,2]diazepine-1(S)-carboxylic acid hydrobromide as a white solid.

NMR: $\delta_H$ (CD$_3$OD, 300 MHz): 1.42 (1H, m), 1.68–1.96 (4H, m), 2.09–2.35 (4H, m), 2.38 (1H, m), 2.60 (1H, m), 2.78–2.96 (2H, m), 3.04 (1H, broad, d), 3.15 (1H, m), 3.48 (1H, m), 4.01 (1H, m), 4.84 (1H, t), about 4.91 (1H, obscured), 7.29 (2H, d) and 7.34 (2H, d).

MS: m/e 492 (2% [M+H]+) and 211 (100).

(C)(ii) A solution of 6 g of tert.butyl 9(S)-[1(S)-tert-.butoxycarbonyl-3-[4-(2-nitroguanidino)phenyl]-propylamino]-octahydro-10-oxo-6H-pyridazo[1,2-a][1,2]diazepine-1(S)-carboxylate in 60 ml of trifluoroacetic acid was stirred at room temperature for 6 hours and then concentrated in vacuo to give a gummy residue containing 9(S)-[1(S)-carboxy-3-[4-(2-nitroguanidino]phenyl]propylamino]-octahydro-10-oxo-6H-pyridazo[1,2-a][1,2]diazepine-1(S)-carboxylic acid trifluoroacetate together with excess trifluoroacetic acid. This gummy residue was dissolved in a mixture of 20 ml of isopropanol and 100 ml of distilled water and the resulting clear solution was hydrogenated over 10% palladium-on-carbon at room temperature and under atmospheric pressure for 24 hours. The catalyst was removed by filtration, the filtrate was treated dropwise with ammonium hydroxide solution until neutral (pH 7), then concentrated in vacuo to a volume of about 50 ml and then left to stand at room temperature for several hours until crystallization was complete. The crystals were filtered off, washed in succession with minimum volumes of distilled water, ethanol and diethyl ether, and finally air-dried to give 4 g of 9(S)-[1(S)-carboxy-3-(4-guanidinophenyl)propylamino]-octahydro-10-oxo-6H-pyridazo[1,2-a][1,2]diazepine-1(S)-carboxylic acid pentahydrate as a white crystalline solid having a melting point of 230°–232° C. (decomposition).

EXAMPLE 2

A solution of 0.45 g of 9(S)-[1(S)-ethoxycarbonyl-3-[4-(2-nitroguanidino)phenyl]propylamino]-octahydro-10-oxo-6H-pyridazo[1,2-a][1,2]diazepine-1(S)-carboxylic acid hydrobromide in a mixture of 20 ml of acetic acid, 5 ml of water and 5 drops of hydrobromic acid was hydrog-enated over 10% palladium-on-carbon at room temperature and under atmospheric pressure for 132 hours. The catalyst was removed by filtration and the filtrate was evaporated. The residue was stirred with 200 ml of anhydrous diethyl ether for 16 hours and the mixture was then filtered to give 0.57 g of 9(S)-[1(S)-ethoxycarbonyl-3-(4-guanidinophenyl)-propylamino]-octahydro-10-oxo-6H-pyridazo[1,2-a][1,2]diazepine-1(S)-carboxylic acid dihydrobromide as an amorphous off-white solid.

NMR: $\delta_H$(CD$_3$OD, 300 MHz): 1.35 (3H, t), 1.44 (1H, m), 1.69–1.94 (4H, m), 2.10–2.35 (4H, m), 2.40 (1H, broad, d), 2.61 (1H, m), 2.83 (1H, m), 2.92 (1H, m), 3.04 (1H, broad, d), 3.18 (1H, m), 3.49 (1H, m), 4.11 (1H, t), 4.35 (2H, m), 4.86–4.95 (2H, obscured), 7.26 (2H, d) and 7.40 (2H, d).

MS: m/e 475 (20%, [M+H]+) and 211 (100).

The 9(S)-[1(S)-ethoxycarbonyl-3-[4-(2-nitroguanidino)phenyl]propylamino]-octahydro-10-oxo-6H-pyridazo[1,2-a][1,2]diazepine-1(S)-carboxylic acid hydrobromide used as the starting material was prepared as follows:

(A) A solution of 2.83 g of tert.butyl 9(S)-aminooctahydro-10-oxo-6H-pyridazo[1,2-a][1,2]diazepine-1(S)-carboxylate, 3.16 g of ethyl 2(R,S)-bromo-4-(4-nitrophenyl)butanoate and 1.01 g of triethylamine in 60 ml of acetonitrile was heated to 80° C. for 15 hours. The solvent was removed by evaporation and the residue was partitioned between water and dichloromethane. The organic solution was evaporated and the resulting oil was chromatographed on silica gel. Elution with toluene/ethyl acetate (3:2) gave 1.78 g of tert.butyl 9(S)-[1(R)-ethoxycarbonyl-3-(4-nitrophenyl)-propylamino]-octahydro-10-oxo-6H-pyridazo[1,2-a][1,2]diazepine-1(S)-carboxylate as a pale yellow oil.

Analysis for C$_{26}$H$_{38}$N$_4$O$_7$: Calculated: C: 60.2; H: 7.4; N: 10.8%; Found: C: 60.1; H: 7.4; N: 10.7%.

Subsequently, using the same solvent system, there were eluted 1.93 g of tert.butyl 9(S)-[1(S)-ethoxycarbonyl-3-(4-nitrophenyl)propylamino[-octahydro-10-oxo-6H-pyridazo[1,2-a][1,2]diazepine-1(S)-carboxylate as a pale yellow oil.

Analysis for C$_{26}$H$_{38}$N$_4$O$_7$: Calculated: C: 60.2; H: 7.4; N: 10.8%; Found: C: 60.2; H: 7.3; N: 10.7%.

(B) A solution of 4.15 g of tert.butyl 9(S)-[1(S)-ethoxycarbonyl-3-(4-nitrophenyl)propylamino]-octahydro-10-oxo-6H-pyridazo[1,2-a][1,2]diazepine-1(S)-carboxylate in 200 ml of ethanol was hydrogenated over 10% palladium-on-carbon at room temperature and under atmospheric pressure for 3 hours. The catalyst was removed by filtration and the volume of the filtrate was reduced to 80 ml by evaporation. 1.76 g of 1-nitroguanyl-3,5-dimethylpyrazole were added and the solution was heated under reflux for 72 hours. The solvent was removed by evaporation and the residue was partitioned between water and dichloromethane. The organic solution was evaporated and the residual oil was chromatographed on two columns of silica gel, with the first column being eluted with ethyl acetate and the second column being eluted with diethyl ether containing 5% by volume of methanol. There were obtained 1.58 g of tert.butyl 9(S)-[1(S)-ethoxycarbonyl-3-[4-(2-nitroguanidino)phenyl]propylamino]-octahydro-10-oxo-6H-pyridazo[1,2-a][1,2]diazepine-1(S)-carboxylate as an orange foam.

Analysis for C$_{27}$H$_{41}$N$_7$O$_7$: Calculated: C: 56.33; H: 7.2; N: 17.0%; Found: C: 56.14; H: 7.0; N: 17.0%.

(C) A solution of 0.95 g of tert.butyl 9(S)-[1(S)-ethoxycarbonyl-3-[4-(2-nitroguanidino)phenyl]-propylamino]-octahydro-10-oxo-6H-pyridazo[1,2-a][1,2]diazepine-1(S)-carboxylate in 4 ml of acetic acid was treated with 12 ml of 45% hydrogen bromide in acetic acid and stirred at 20° C. for 1 hour. The solution was poured into 500 ml of anhydrous diethyl ether, stirred for 1 hour and then filtered to give 0.89 g of 9(S)-[1(S)-ethoxycarbonyl-3-[4-(2-nitroguanidino)-phenyl]propylamino]-octahydro-10-oxo-6H-pyridazo[1,2-a][1,2]diazepine-1(S)-carboxylic acid hydrobromide as an amorphous white solid. NMR: $\delta_H$ (CD$_3$OD, 300 MHz): 1.33 (3H, t), 1.43 (1H, m), 1.66–1.98 (4H, m), 2.06–2.35 (4H, m), 2.40 (1H, broad, d), 2.60 (1H, m), 2.73–2.96 (2H, m), 3.02 (1H, broad, d), 3.15 (1H, m), 3.47 (1H, m), 4.07 (1H, t), 4.33 (2H, m), 4.80–5.00 (2H, obscured), 7.29 (2H, d) and 7.35 (2H, d).

MS: m/e 520 (2% [M+H]+) and 211 (100).

EXAMPLE 3

A solution of 0.39 g 9(S)-[1(S)-(n-decyloxycarbonyl)-3-[4-(2-nitroguanidino)phenyl]propylamino]-octahydro-10-oxo-6H-pyridazo[1,2-a][1,2]diazepine-1(S)-carboxylic acid hydrobromide in a mixture of 16 ml of acetic acid, 4 ml of water and 4 drops of hydrobromic acid was hydrogenated over 10% palladium-on-carbon at room temperature and at atmospheric pressure for 48 hours. The catalyst was removed by filtration and the filtrate was freeze-dried. The resulting solid was lyophilized from water to give 0.34 g of 9(S)-[1(S)-(n-decyloxycarbonyl)-3-(4-guanidinophenyl)propylamino]-octahydro-10-oxo-6H-pyridazo[1,2-a][1,2]diazepine-1(S)-carboxylic acid dihydrobromide as a light tan amorphous solid.

NMR: δH (CD$_3$OD, 300 MHz): 0.89 (3H, m), 1.21–1.50 (17H, m), 1.66–1.99 (4H, m), 2.03–2.45 (5H, m), 2.61 (1H, m), 2.74–2.98 (2H, m), 3.04 (1H, broad, d), 3.18 (1H, m), 3.49 (1H, m), 4.13 (1H, t), 4.20–4.40 (2H, m), 4.82–5.00 (2H, obscured), 7.26 (2H, d) and 7.40 (2H, d).

MS: m/e 587 [13% (M+H)$^+$] and 211 (100).

The 9(S)-[1(S)-(n-decyloxycarbonyl)-3-[4-(2-nitroguanidinophenyl]propylamino]-octahydro-10-oxo-6H-pyridazo[1,2-a][1,2]diazepine-1(S)-carboxylic acid hydrobromide used as the starting material was prepared as follows:

(A) A solution of 2.07 g of tert.butyl 9(S)-[1(S)-ethoxycarbonyl-3-(4-nitrophenyl)propylamino]-octahydro-10 oxo-6H-pyridazo[1,2-a][1,2]diazepine-1(S)-carboxylate, prepared as described in Example 2(A), in 10 ml of ethanol was treated with 10 ml of 1M aqueous sodium hydroxide solution. The resulting solution was stirred at 20° C. for 5 hours and then diluted with water. The ethanol was removed by evaporation. The aqueous solution was adjusted to pH 4 and then extracted with dichloromethane. The organic solution was evaporated to give a yellow foam. 0.49 g of the foam was added to a solution of 0.81 g of 1,1'-carbonyldiimidazole and 1.42 g of methyl iodide in 5 ml of dichloromethane which had been stirred at 20° C. for 3 hours. 0.158 g of n-decanol was added and the solution was stirred at 20° C. for a further 24 hours. The mixture was partitioned between dichloromethane and dilute hydrochloric acid. The organic solution was evaporated and the resulting oil was chromatographed on silica gel. Elution with diethyl ether/n-hexane (2:1) gave 0.19 g of tert.butyl 9(S)-[1(S)-(n-decyloxycarbonyl)-3-(4-nitrophenyl)-propylamino]-octahydro-10-oxo-6H-pyridazo-[1,2-a][1,2]diazepine-1(S)-carboxylate as a yellow oil.

NMR: δ$_H$(CDCl$_3$, 300 MHz): 1.88 (3H, m), 1.17–1.41 (17H, m), 1.48 (9H, s), 1.57–1.82 (4H, m), 1.87–2.12 (4H, m), 2.30 (1H, m), 2.50 (1H, m), 2.82–3.13 (4H, m), 3.35 (1H, t), 3.42 (1H, m), 4.05–4.22 (3H, m), 4.94 (1H, m), 7.37 (2H, d) and 8.14 (2H, d).

MS: m/e 630 (3%, M$^+$), 501 (37), 211 (56), 179 (83), 143 (87) and 57 (100).

(B) A solution of 2.017 g of tert.butyl 9(S)-[1(S)-(n-decyloxycarbonyl)-3-(4-nitrophenyl)propylamino]-octahydro-10-oxo-6H-pyridazo[1,2-a][1,2]diazepine-1(S)-carboxylate in 25 ml of ethanol was hydrogenated over 10% palladium-on-carbon at room temperature and under atmospheric pressure for 18 hours. The catalyst was removed by filtration and the filtrate was evaporated to give 1.9 g of tert.butyl 9(S)-[3-(4-aminophenyl)-1(S)-(n-decyloxycarbonyl)propylamino]-octahydro-10-oxo-6H-pyridazo[1,2-a][1,2]diazepine-1(S)-carboxylate as a colorless oil.

Analysis for C$_{34}$H$_{56}$N$_4$O$_5$: Calculated: C: 68.0; H: 9.4; N: 9.3%; Found: C: 68.1; H: 9.7; N: 9.2%.

(C) A solution of 1.67 g of tert.butyl 9(S)-[3-(4-aminophenyl)-1(S)-(n-decyloxycarbonyl)propylamino]-octahydro-10-oxo-6H-pyridazo[1,2-a][1,2]diazepine-1(S)-carboxylate and 0.611 g of 1-nitroguanyl-3,5-dimethylpyrazole in 25 ml of ethanol was heated under reflux for 72 hours. The solvent was removed by evaporation and the residue was chromatographed on silica gel using 3% methanol in diethyl ether for the elution. Material of Rf 0.4 (5% methanol in diethyl ether) was partitioned between diethyl ether/n-hexane and water. The organic phase was separated and evaporated to give 0.76 g of tert.butyl 9(S)-[1(S)-[n-decyloxycarbonyl)-3-[4-(2-nitroguanidino)phenyl]propylamino]-octahydro-10-oxo-6H-pyridazo[1,2-a][1,2]diazepine-1(S)-carboxylate as an off-white foam.

Analysis for C$_{35}$H$_{57}$N$_7$O$_7$: Calculated: C: 61.1; H: 8.35; N: 14.25%; Found: C: 61.0; H: 8.45; N: 14.10%.

(D) A solution of 0.70 g of tert.butyl 9(S)-[1(S)-(n-decyloxycarbonyl)-3-[4-(2-nitoguanidino)phenyl]-propylamino]-octahydro-10-oxo-6H-pyridazo[1,2-a][1,2]diazepine-1(S)-carboxylate in 2.5 ml of acetic acid was treated with 8.0 ml of 45% hydrogen bromide in acetic acid and the solution was stirred at 20° C. for 1 hour. The solution was poured into 200 ml of anhydrous diethyl ether, stirred for 2 hours and then filtered to given 0.54 g of 9(S)-[1(S)-(n-decyloxycarbonyl)- -[4-(2-nitroguanidino)phenyl]propylamino]-octahydro-10-oxo-6H-pyridazo[1,2-a][1,2]diazepine-1(S)-carboxylic acid hydrobromide as an off-white amorphous solid.

Analysis for C$_{31}$H$_{49}$N$_7$O$_7$.HBr: Calculated: C: 52.20; H: 7.07; N: 13.75; Br; 11.21% Found: C: 51.85; H: 6.95; N: 13.51; Br; 11.23%.

EXAMPLE 4

A solution of 0.34 g of 9(S)-[1(S)-[[2-(1-adamantyl)ethoxy]carbonyl]-3-[4-(2-nitroguanidino)phenyl]-propylamino]-octahydro-10-oxo-6H-pyridazo[1,2-a][1,2]-1(S)-carboxylic acid hydrobromide in 16 ml of acetic acid and 4 ml of water containing a few drops of hydrobromic acid was hydrogenated over 10% palladium-on-carbon at room temperature and under atmospheric pressure for 48 hours. The catalyst was removed by filtration and the filtrate was lyophilized to give 0.4 g of 9(S)-[1(S)-[[2-(1-adamantyl)ethoxy]carbonyl]-3-(4-guanidinophenyl)propylamino]-octahydro-10-oxo-6H-pyridazo[1,2-a][1,2]diazepine-1(S)-carboxylic acid dihydrobromide as a white amorphous solid.

NMR: δ$_H$ (CD$_3$OD, 300 MHz): 1.51 (3H, m), 1.60 (6H, s), 1.64–2.03 (13H, m), 2.06–2.36 (4H, m), 2.43 (1H, m), 2.60 (1H, m), 2.74–2.97 (2H, m), 3.04 (1H, m), 3.15 (1H, m), 3.52 (1H, m), 4.02 (1H, t), 4.36 (2H, m), 4.77–5.07 (2H, obscured), 7.25 (2H, d) and 7.38 (2H, d).

MS: m/e 609 (20% [M+H]$^+$) and 211 (100).

The 9(S)-[1(S)-[[2-adamantyl)ethoxy]carbonyl]-3-[4-(2-nitroguanidino)phenyl]propylamino]-octahydro-10-oxo-6H-pyridazo[1,2-a[1,2]diazepine-1(S)-carboxylic acid hydrobromide used as the starting material was prepared as follows:

(A) A solution of 2.95 g of tert.butyl 9(S)-[1(S)-ethoxycarbonyl-3-(4-nitrophenyl)propylamino]-octahydro-10-oxo-6H-pyridazo[1,2-a][1,2-]diazepine-1(S)-carboxylate in 32 ml of ethanol was treated with 28.5 ml of 0.5M aqueous sodium hydroxide solution at 20° C. for 16 hours. The mixture was diluted with water and the ethanol was removed by evaporation. The aqueous solution was adjusted to pH 6 and extracted with dichloromethane. The organic solution was then evaporated to give 2.62 g of a yellow solid. 2.3 g of this solid were added to a solution of 3.80 g of 1,1'-carbonyldiimidazol and 6.66 g of methyl iodide in 25 ml of dry dichloromethane which had been stirred at 20° C. for 3 hours. After 1 hour, 0.84 g of 1-adamantane ethanol was added and the solution was then stirred at 20° C. for 16 hours. The mixture was then filtered, the filtrate was diluted with dichloromethane, washed in sequence with 2M aqueous hydrochloric acid, water, 5% aqueous sodium bicarbonate solution and water, and then evaporated. Chromatography on two columns of silica gel, using chloroform/methanol/acetate/acid/water (120:15:3:2) for the elution of the first column and diethyl ether for the elution of the second column, gave 1.84 g of tert.butyl 9(S)-[1(S)-[[2-(1-adamantylethoxy]-carbonyl]-3-(4-nitrophenyl)propylamino]-octahydro-10-oxo-6H-pyridazo[1,2-a][1,2]diazepine-1(S)-carboxylate as a pale yellow oil.

(B) A solution of 1.84 g of tert.butyl 9(S)-[1(S)-[[2-(1-adamantyl)ethoxy]carbonyl]-3-(4-nitrophenyl)-propylamino]-10-oxo-6H-pyridazo[1,2-a][1,2]diazepine-1(S)-carboxylate in 25 ml of ethanol was hydrogenated over 10% palladium-on-carbon at room temperature and under atmospheric pressure for 16 hours. The catalyst was removed by filtration and the filtrate was evaporated to give 1.8 g of a pale yellow oil. A solution of 1.6 g of this oil and 0.56 g of 1-nitroguanyl-3,5-dimethylpyrazole in 20 ml of ethanol was heated under reflux for 72 hours while stirring. The mixture was then evaporated and the residue was chromatographed on two columns of silica gel, using diethyl ether containing 3% by volume of methanol for the elution of the first colum and ethyl acetate for the elution of the second column. There was obtained 0.50 g of tert.butyl 9(S)-[1(S)-[[2-(1-adamantyl)ethoxy]carbonyl]-3-[4-(2-nitroguanidino)phenyl]propylamino]-octahydro-10-oxo-6H-pyridazo[1,2-a][1,2]diazepine-1(S)-carboxylate in the form of a white foam.

Analysis for $C_{37}H_{55}N_7O_7$: Calculated: C: 62.60; H: 7.81; N: 13.81%; Found: C: 62.52; H: 7.82; N: 13.86%.

(C) A solution of 0.45 g of tert.butyl 9(S)-[1(S)-[[2-(1-adamantyl)ethoxy]carbonyl]-3-[4-(2-nitroguanidino)-phenyl]propylamino]-octahydro-10-oxo-6H-pyridazo[1,2-a][1,2]diazepine-1(S)-carboxylate in 1.5 ml of acetic acid was treated with 5 ml of 45% hydrogen bromide in acetic acid and the mixture was stirred at 20° C. for 1 hour. The solution was poured into 200 ml of anhydrous diethyl ether, stirred for 1 hour and then filtered to give 0.53 g of 9(S)-[1(S)-[[2-(1-adamantyl)ethoxy]carbonyl]-3-[4-(2-nitroguanidino)phenyl]-propylamino]-octahydro-10-oxo-6H-pyridazo[1,2-a][1,2]diazepine-1(S)-carboxylic acid hydrobromide as a white solid.

NMR: $\delta_H$ (CD$_3$OD, 300 MHz): 1.50 (3H, m), 1.58 (6H, s), 1.63–2.00 (13H, m), 2.07–2.36 (4H, m), 2.41 (1H, m), 2.61 (1H, m), 2.74–2.98 (2H, m), 3.05 (1H, broad, d), 3.17 (1H, m), 3.48 (1H, m), 4.06 (1H, t), 4.33 (2H, m), 4.82–4.97 (2H, obscured) and 7.32 (4H, m).

MS: m/e 654 (3% [M+H]$^+$) and 211 (100).

EXAMPLE 5

A solution of 0.48 g of 9(S)-[N-benzyl-1(S)-ethoxycarbonyl)-3-[4-(2-nitroguanidino)phenyl]-propylamino]-octahydro-10-oxo-6H-pyridazo[1,2-a][1,2]diazepine-1(S)-carboxylic acid pivaloyloxy methyl ester in 20 ml of acetic acid and 5 ml of water was hydrogenated over 10% palladium-on-carbon at room temperature and under atmospheric pressure for 30 hours. The catalyst was removed by filtration and the filtrate was lyophilized. The resulting gum was chromatographed on silica gel using chloroform/methanol/acetic acid/water (120:15:3:2) for the elution to give 0.19 g of 9(S)-[1(S)-ethoxycarbonyl-3-(4-guanidinophenyl)propylamino]-octahydro-10-oxo-6H-pyridazo[1,2-a][1,2]diazepine-1(S)-carboxylic acid pivaloyloxy methyl ester acetate as an off-white amorphous solid.

Analysis for $C_{29}H_{44}N_6O_7.1:1C_2H_4O_2$: Calculated: C: 57.39; H: 7.46; N: 12.95%; Found: C: 56.90; H: 7.52; N: 12.87%.

NMR: $\delta_H$ (CDCl$_3$, 300 MHz): 1.21 (9H, s), 1.28 (3H, t), 1.34–2.12 (9H, m), 1.97 (3H, s), 2.28 (1H, m), 2.32 (1H, m), 7.74 (2H, m), 2.95 (1H, m), 3.08 (1H, m), 3.31 (1H, t), 3.35 (1H, m), 4.14 (1H, m), 4.20 (2H, m), 5.02 (1H, m), 5.74 (1H, d), 5.83 (1H, d), 7.14 (2H, d) and 7.24 (2H, d).

MS: m/e 589 (30%, [M+H]$^+$), 211 (80) and 149 (100).

The 9(S)-[N-benzyl-1(S)-ethoxycarbonyl-3-[4-(2-nitroguanidino)phenyl]propylamino]-octahydro-10-oxo-6H-pyridazo[1,2-a][1,2]diazepine-1(S)-carboxylic acid pivaloyloxy methyl ester used as the starting material was prepared as follows:

(A) 5.09 g of tert.butyl 9(S)-amino-octahydro-10-oxo-6H-pyridazo[1,2-a][1,2]diazepine-1(S)-carboxylate, 1.91 g of benzaldehyde and 3 g of 3A molecular sieve in 54 ml of ethanol were stirred for 3 hours and then hydrogenated over 5% palladium-on-carbon at room temperature and under atmospheric pressure for 1.75 hours. The catalyst was removed by filtration and the filtrate was evaporated. Chromatography of the residue on silica gel using diethyl ether/methanol (39:1) for the elution gave 5.25 g of tert.butyl 9(S)-benzylamino-octahydro-10-oxo-6H-pyridazo[1,2-a][1,2]diazepine-1(S)-carboxylate as a pale yellow oil.

NMR: $\delta_H$ (CDCl$_3$, 300 MHz): 1.37 (1H, m), 1.47 (10H, m), 1.65–1.84 (3H, m), 1.92 (1H, m), 2.07 (1H, m), 2.31 (1H, broad, d), 2.52 (1H, m), 2.94 (1H, broad, d), 3.07 (1H, m), 3.28 (1H, broad, s), 3.41 (1H, m), 3.68 (1H, d), 3.89 (1H, d), 4.23 (1H, t), 4.97 (1H, m) and 7.20–7.44 (5H, m).

(B) A solution of 1.87 g of tert.butyl 9(S)-benzylamino-octahydro-10-oxo-6H-pyridazo[1,2-a][1,2]diazepine-1(S)-carboxylate, 1.93 g of ethyl 2(R)-trifluoromethanesulphonyloxy-4-(4-nitrophenyl)-butanoate and 0.7 g of triethylamine in 5 ml of acetonitrile was stirred at 20° C. for 2 hours. A further 0.2 g of ethyl 2(R)-trifluoromethanesulphonyloxy-4-(4-nitrophenyl)butanoate and 0.05 g of triethylamine were added and the solution was then left to stand at 20° C. for 16 hours. The solvents were removed by evaporation and the residue was partitioned between water and dichloromethane. Evaporation of the organic solution followed by chromatography on silica gel using diethyl ether/n-hexane (1:1) for the elution gave 2.44 g of tert-.butyl 9(S)-[N-benzyl-1(S)-ethoxycarbonyl-3-(4-nitrophenyl)propylamino]-octahydro-10-oxo-6H-pyridazo[1,2-a][1,2]diazepine-1(S)-carboxylate as a pale yellow oil.

Analysis for $C_{33}H_{44}N_4O_7$: Calculated: C: 65.11; H: 7.29; N: 9.20%; Found: C: 65.41; H: 7.15; N: 9.20%.

(C) A solution of 2.0 g of tert.butyl 9(S)-[N-benzyl-1(S)-ethoxycarbonyl-3-(4-nitrophenyl)propylamino]- octahydro-10-oxo-6H-pyridazo[1,2-a][1,2]diazepine-1(S)-carboxylate in 10 ml of trifluoroacetic acid was stirred at 20° C. for 2.5 hours and then left to stand at 0° C. for 16 hours. 20 ml of toluene were added and the solution was evaporated. The residue was dissolved in dichloromethane, washed with water and sodium chloride solution, and then evaporated. Chromatography on silica gel using dichloromethane/methanol (19:1) for the elution gave 0.9 g of 9(S)-[N-benzyl-1(S)-ethoxycarbonyl-3-(4-nitrophenyl)propylamino]-octahydro-10-oxo-6H-pyridazo[1,2-a][1,2]diazepine-1(S)-carboxylic acid as a pale yellow oil.

NMR: $\delta_H$(CDCl$_3$, 300 MHz): 1.33 (4H, m), 1.62 (1H, m), 1.71–2.09 (7H, m), 2.40 (1H, m), 2.45–2.59 (2H, m), 2.66 (1H, m), 3.00 (1H, broad, d), 3.17 (1H, m), 3.29 (2H, m), 4.01–4.20 (2H, m), 4.23 (1H, d), 4.39 (1H, d), 4.75 (1H, t), 4.84 (1H, m), 7.13 (2H, d), 7.19–7.40 (5H, m) and 8.04 (2H, d).

MS: m/e 553 (2%, [M+H]+) and 211 (100).

(D) A solution of 2.68 g of 9(S)-[N-benzyl-1(S)-ethoxycarbonyl-3-(4-nitrophenyl)propylamino]-octahydro-10-oxo-6H-pyridazo[1,2-a][1,2]diazepine-1(S)-carboxylic acid in 10 ml of acetone was treated with 0.32 g of potassium hydroxide in 0.5 ml of water, 0.73 g of chloromethyl pivalate and 0.12 g of sodium iodide. The mixture was heated under reflux for 5 hours and then partitioned between water and dichloromethane. The organic phase was evaporated and the residue was chromatographed on silica gel using diethyl ether/n-hexane (1:1) for the elution, to give 1.72 g of 9(S)-[N-benzyl-1(S)-ethoxycarbonyl-3-(4-nitrophenyl)propylamino]-octahydro-10-oxo-6H-pyridazo[1,2-a][1,2]diazepine-1(S)-carboxylic acid pivaloyloxy methyl ester as a pale yellow oil.

Analysis for C$_{35}$H$_{46}$N$_4$O$_9$: Calculated: C: 63.05; H: 6.95; N: 8.40%; Found: C: 62.81; H: 6.84; N: 8.22%.

(E) A mixture of 1.66 g of 9(S)-[N-benzyl-1(S)-ethoxycarbonyl-3-(4-nitrophenyl)propylamino]-octahydro-10-oxo-6H-pyridazo[1,2-a][1,2]diazepine-1(S)-carboxylic acid pivaloyloxy methyl ester and 0.97 g of powdered zinc in 35 ml of 85% acetic acid was stirred at 20° C. for 3 hours. Excess zinc was removed by filtration and the filtrated was evaporated. The residue was partitioned between water and dichloromethane and the organic phase was evaporated. The resulting oil was taken up in 25 ml of ethanol and the solution was treated with 0.55 g of 1-nitroguanyl-3,5-dimethylpyrazole. The solution was then heated under reflux for 72 hours while stirring. A further 0.55 g of 1-nitroguanyl-3,5-dimethylpyrazole was added and the mixture was heated under reflux for a further 24 hours while stirring. The mixture was then evaporated to dryness and the residue was chromatographed on silica gel using diethyl ether/methanol (39:1) for the elution to give 0.58 g of 9(S)-[N-benzyl-1(S)-ethoxycarbonyl-3-[4-(2-nitroguanidino)phenyl]propylamino]-octahydro-1oxo-6H-pyridazo[1,2-a][1,2]diazepine-1(S)-carboxylic acid pivaloyloxymethyl ester as an off-white foam.

Analysis for C$_{36}$H$_{49}$N$_7$O$_9$: Calculated: C: 59.74; H: 6.82; N: 13.55%; Found: C: 59.75; H: 6.85; N: 13.38%.

The following additional Examples illustrate pharmaceutical preparations containing 9(S)-[1(S)-carboxy-3-(4-guanidinophenyl)propylamino]-octahydro-10-oxo-6H-pyridazo[1,2-a][1,2]diazepine-1(S)-carboxylic acid dihydrobromide (Compound A) as the active ingredient.

EXAMPLE A

Tablets containing the following ingredients can be produced in a conventional manner:

| Ingredient | Per tablet |
| --- | --- |
| Compound A | 10.0 mg |
| Lactose | 125.0 mg |
| Maize starch | 75.0 mg |
| Talc | 4.0 mg |
| Magnesium stearate | 1.0 mg |
| Tablet weight | 215.0 mg |

EXAMPLE B

Capsules containing the following ingredients can be produced in a conventional manner:

| Ingredient | Per capsule |
| --- | --- |
| Compound A | 25.0 mg |
| Lactose | 150.0 mg |
| Maize starch | 20.0 mg |
| Talc | 5.0 mg |
| Capsule fill weight | 200.0 mg |

We claim:
1. A pyridazodiazepine compound of the formula

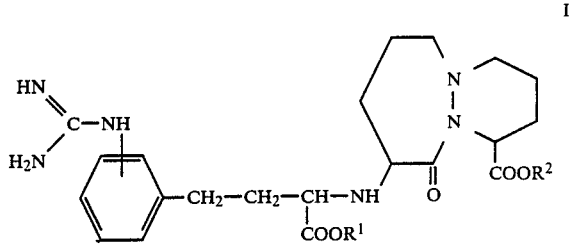

I wherein R$^1$ and R$^2$ each independently are hydrogen, C$_1$–C$_{10}$-alkyl, adamantyl-(C$_1$–C$_4$-alkyl) or (C$_2$–C$_6$-alkanoyloxy)-(C$_1$–C$_4$-alkyl), as well as pharmaceutically acceptable salts thereof.

2. A compound according to claim 1, wherein R$^1$ is hydrogen, C$_1$–C$_{10}$-alkyl or adamantyl-(C$_1$–C$_4$-alkyl).

3. A compound according to claim 2, wherein R$^1$ is hydrogen, ethyl, n-decyl or 1-adamantylethyl.

4. A compound according to claim 1, wherein R$^2$ is hydrogen or (C$_2$–C$_6$-alkanoyloxy)-(C$_1$–C$_{14}$-alkyl).

5. A compound according to claim 4, wherein R$^2$ is hydrogen or pivaloyloxymethyl.

6. A compound according to claim 1, wherein the H$_2$N—C(NH)—NH—group is situated in the para-position of the phenyl ring.

7. A compound according to claim 1, wherein R$^1$ is hydrogen, ethyl, n-decyl or 1-adamantylethyl, R$^2$ is hydrogen or pivaloyloxymethyl, and the H$_2$N—C(NH)—NH—group is situated in the para-position of the phenyl ring.

8. A compound according to claim 1 which is 9(S)-[1(S)-carboxy-3-(4-guanidinophenyl)propylamino]-octahydro-10-oxo-6H-pyridazo[1,2-a][1,2]diazepine-1(S)-carboxylic acid, or a pharmaceutically acceptable salt thereof.

9. A compound according to claim 1 which is 9(S)-[1(S)-carboxy-3-(4-guanidinophenyl)propylamino]- octahydro-10-oxo-6H-pyridazo[1,2-a][1,2]diazepine-1(S)-carboxylic acid dihydrobromide.

10. A compound according to claim 1 which is 9(S)-[1(S)-ethoxycarbonyl-3-(4-guanidinophenyl)propylamino]-octahydro-10-oxo-6H-pyridazo[1,2-a][1,2]diazepine-1(S)-carboxylic acid, or a pharmaceutically acceptable salt thereof.

11. A compound according to claim 1 which is 9(S)-[1(S)-(n-decyloxycarbonyl)-3-(4-guanidinophenyl)propylamino]-octahydro-10-oxo-6H-pyridazo[1,2-a][1,2]diazepine-1(S)-carboxylic acid, or a pharmaceutically acceptable salt thereof.

12. A compound according to claim 1 which is 9(S)-[1(S)-[[2-(1-adamantyl)ethoxy]carbonyl]-3-(4-guanidinophenyl)propylamino]-octahydro-10-oxo-6H-pyridazo[1,2-a][1,2]diazepine-1(S)-carboxylic acid, or a pharmaceutically acceptable salt thereof.

13. A compound according to claim 1 which is 9(S)-[1(S)-ethoxycarbonyl-3-(4-guanidinophenyl)propylamino]-octahydro-10-oxo-6H-pyridazo[1,2-a][1,2]diazepine-1(S)-carboxylic acid pivaloyloxymethyl ester, or a pharmaceutically acceptable salt thereof.

14. A pharmaceutical composition for treating or preventing high blood pressure containing an amount effective to treat or prevent high blood pressure of a compound having the formula

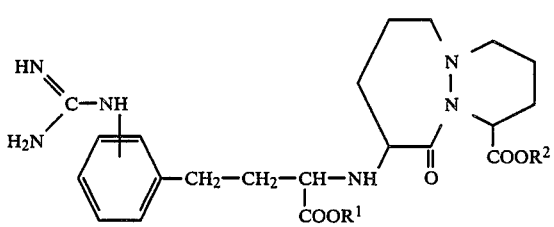

wherein $R^1$ and $R^2$ each independently are hydrogen, $C_1$–$C_{10}$-alkyl, adamantyl-($C_1$–$C_4$-alkyl) or ($C_2$–$C_6$-alkanoyloxy)-($C_1$–$C_4$-alkyl), or a pharmaceutically acceptable salt thereof, and one or more therapeutically inert excipients.

15. A composition according to claim 14, wherein $R^1$ is hydrogen, $C_1$–$C_{10}$-alkyl or adamantyl-($C_1$–$C_4$-alkyl).

16. A composition according to claim 15, wherein $R^1$ is hydrogen, ethyl, n-decyl or 1-adamantylethyl.

17. A composition according to claim 14, wherein $R^2$ is hydrogen or ($C_2$–$C_6$-alkanoyloxy)-($C_1$–$C_4$-alkyl).

18. A composition according to claim 17, wherein $R^2$ is hydrogen or pivaloyloxymethyl.

19. A composition according to claim 14, wherein the $H_2N$—C(NH)—NH— group is situated in the para-position of the phenyl ring.

20. A composition according to claim 14, wherein $R^1$ is hydrogen, ethyl, n-decyl or 1-adamantylethyl, $R^2$ is hydrogen or pivaloyloxymethyl, and the $H_2N$—C(NH)—NH— group is situated in the para-position of the phenyl ring.

21. A composition according to claim 14 in which the active compound is 9(S)-[1(S)-Carboxy-3-(4-guanidinophenyl)propylamino]-octahydro-10-oxo-6H-pyridazo[1,2-a][1,2]diazepine-1(S)-carboxylic acid or a pharmaceutically acceptable salt thereof.

22. A composition according to claim 14 in which the active compound is 9(S)-[1(S)-carboxy-3-(4-guanidinophenyl)propylamino]-octahydro-10-oxo-6H-pyridazo[1,2-a][1,2]diazepine-1(S)-carboxylic acid dihydrobromide.

23. A composition according to claim 14 in which the active compound is 9(S)-[1(S)-ethoxycarbonyl-3-(4-guanidinophenyl)propylamino]-octahydro-10-oxo-6H-pyridazo[1,2-a][1,2]-diazepine-1(S)-carboxylic acid or a pharmaceutically acceptable salt thereof.

24. A composition according to claim 14 in which the active compound is 9(S)-[1(S)-(n-decyloxycarbonyl)-3-(4-guanidinophenyl)propylamino]-octahydro-10-oxo-6H-pyridazo[1,2-a][1,2]-diazepine-1(S)-carboxylic acid or a pharmaceutically acceptable salt thereof.

25. A composition according to claim 14 in which the active compound is 9(S)-[[2-(1-adamantyl)ethoxy]carbonyl]-3-(4-guanidinophenyl)propylamino]-octahydro-10-oxo-6H-pyridazo[1,2-a][1,2]diazepine-1(S)-carboxylic acid or or a pharmaceutically acceptable salt thereof.

26. A composition according to claim 14 in which the active compound is 9(S)-[1(S)-ethoxycarbonyl-3-(4-guanidinophenyl)propylamino]-octahydro-10-oxo-6H-pyridazo[1,2-a][1,2]-diazepine-1(S)-carboxylic acid pivaloyloxymethyl ester or a pharmaceutically acceptable salt thereof.

27. A method of treating or preventing high blood pressure which comprises administering to a patient requiring such treatment an effective amount of a pyridazodiazepine derivative of the formula

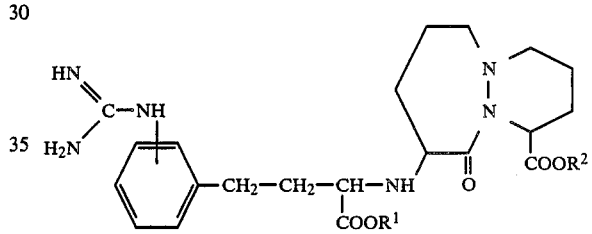

wherein $R^1$ and $R^2$ each independently are hydrogen, $C_1$–$C_{10}$-alkyl, adamantyl-($C_1$–$C_4$-alkyl) or ($C_2$–$C_6$-alkanoyloxy)-($C_1$–$C_4$-alkyl), or a pharmaceutically acceptable salt thereof.

28. A method according to claim 27, wherein $R^1$ is hydrogen, $C_1$–$C_{10}$-alkyl or adamantyl-($C_1$–$C_4$-alkyl).

29. A method according to claim 29, wherein $R^1$ is hydrogen, ethyl, n-decyl or 1-adamantylethyl.

30. A method according to claim 27, wherein $R^2$ is hydrogen or ($C_2$–$C_6$-alkanoyloxy)-($C_1$–$C_4$-alkyl).

31. A method according to claim 30, wherein $R^2$ is hydrogen or pivaloyloxymethyl.

32. A method according to claim 27, wherein the $H_2N$—C(NH)—NH— group is situated in the para-position of the phenyl ring.

33. A method according to claim 27, wherein $R^1$ is hydrogen, ethyl, n-decyl or 1-adamantylethyl, $R^2$ is hydrogen or pivaloyloxymethyl, and the $H_2N$—C(NH)—NH— group is situated in the para-position of the phenyl ring.

34. A method according to claim 27 in which the compound is 9(S)-[1(S)-carboxy-3-(4-guanidinophenyl)propylamino]-octahydro-10-oxo-6H-pyridazo[1,2-a][1,2]diazepine-1(S)-carboxylic acid or a pharmaceutically acceptable salt thereof.

35. A method according to claim 27 in which the compound is 9(S)-[1(S)-carboxy-3-(4-guanidinophenyl)propylamino]-octahydro-10-oxo-6H-pyridazo[1,2-a][1,2]diazepine-1(S)-carboxylic acid dihydrobromide.

36. A method according to claim 27 in which the compound is 9(S)-[1(S)-ethoxycarbonyl-3-(4-guanidinophenyl)propylamino]-octahydro-10-oxo-6H-pyridazo[1,2-a][1,2]-diazepine-1(S)-carboxylic acid or a pharmaceutically acceptable salt thereof.

37. A method according to claim 27 in which the compound is 9(S)-[1(S)-(n-decyloxycarbonyl)-3-(4-guanidinophenyl)propylamino]-octahydro-10-oxo-6H-pyridazo[1,2-a][1,2]-diazepine-1(S)-carboxylic acid or a pharmaceutically acceptable salt thereof.

38. A method according to claim 27 in which the compound is 9(S)-[1(S)-[[2-(1-adamantyl)ethoxy]carbonyl]-3-(4-guanidinophenyl)propylamino]-octahydro-10-oxo-6H-pyridazo[1,2-a][1,2]diazepine-1(S)-carboxylic acid or a pharmaceutically acceptable salt thereof.

39. A method according to claim 27 in which the compound is 9(S)-[1(S)-ethoxycarbonyl-3-(4-guanidinophenyl)propylamino]-octahydro-10-oxo-6H-pyridazo[1,2-a][1,2]diazepine-1(S)-carboxylic acid pivaloyloxymethyl ester or a pharmaceutically acceptable salt thereof.

* * * * *

UNITED STATES PATENT AND TRADEMARK OFFICE
CERTIFICATE OF CORRECTION

PATENT NO. : 4,757,069

DATED : July 12, 1988

INVENTOR(S) : GEOFFREY LAWTON AND SALLY REDSHAW

It is certified that error appears in the above-identified patent and that said Letters Patent is hereby corrected as shown below:

In column 18, line 51, the term "$(C_1-C_{14}-alkyl)$" should read -- $(C_1-C_4-alkyl)$ --.

In column 20, line 14, the term "9(s)-[[2-(1-adamantyl)ethoxy]car-" should be -- 9(s)-[1(S)-[[2-(1-adamantyl)ethoxy]car- --; and on line 17, the second occurrence of the word "or" should be deleted.

Signed and Sealed this

Twenty-fourth Day of October, 1989

Attest:

DONALD J. QUIGG

Attesting Officer

Commissioner of Patents and Trademarks